US008093436B2

(12) United States Patent
Khachik

(10) Patent No.: US 8,093,436 B2
(45) Date of Patent: Jan. 10, 2012

(54) PROCESS FOR SYNTHESIS OF (3R,3'R)-ZEAXANTHIN AND (3R,3'S;MESO)-ZEAXANTHIN FROM (3R,3'R,6'R)-LUTEIN VIA (3R)-3',4'-ANHYDROLUTEIN

(75) Inventor: Frederick Khachik, Rockville, MD (US)

(73) Assignee: University of Maryland, College Park, College Park, MD (US)

( * ) Notice: Subject to any disclaimer, the term of this patent is extended or adjusted under 35 U.S.C. 154(b) by 123 days.

(21) Appl. No.: 12/406,543

(22) Filed: Mar. 18, 2009

(65) Prior Publication Data

US 2009/0238933 A1    Sep. 24, 2009

Related U.S. Application Data

(60) Provisional application No. 61/037,872, filed on Mar. 19, 2008.

(51) Int. Cl.
*C07C 35/21*    (2006.01)

(52) U.S. Cl. ........................................................ 568/816
(58) Field of Classification Search .................... 568/816
See application file for complete search history.

(56) References Cited

U.S. PATENT DOCUMENTS

| 4,153,615 | A | 5/1979 | Saucy |
| 5,382,714 | A | 1/1995 | Khachik |
| 5,523,494 | A | 6/1996 | Torres-Cardona et al. |
| 5,780,693 | A | 7/1998 | Bernhard et al. |
| 5,998,678 | A | 12/1999 | Sanroma Virgili et al. |
| 6,818,798 | B1 | 11/2004 | Khachik |
| 6,911,564 | B2 * | 6/2005 | Khachik ........................ 568/816 |
| 7,115,786 | B2 | 10/2006 | Khachik |
| 2009/0264681 | A1 | 10/2009 | Khachik et al. |

FOREIGN PATENT DOCUMENTS

| WO | WO 97/31894 A1 | 9/1997 |
| WO | WO 99/03830 A1 | 1/1999 |

OTHER PUBLICATIONS

U.S. Appl. No. 12/484,703, Unpublished, Khachik and Chang.
Bell H., et al., "The Reduction of Organic Halogen Compounds by Sodium Borohydride", *The Journal of Organic Chemistry*, 34: 3923-3926 (1969), American Chemical Society, Washington, DC, USA.
Brown, H.C. and Ramachandran, V.P., "Versatile Alpha-Pinene-Based Borane Reagents for Asymmetric Syntheses," *Journal of Organometallic Chemistry*, 500:1-19 (1995), Elsevier Science, Lausanne, Switzerland.
Khachik F., et al., "Transformations of Selected Carotenoids in Plasma, Liver, and Ocular Tissues of Humans and in Nonprimate Animal Models," *Investigative Ophthalmology & Visual Science*, 43: 3383-3392 (2002), The Association for Research in Vision and Ophthalmology, Rockville, MD, USA.
Khachik F., "An Efficient Conversion of (3R,3'R,6'R)-Lutein to (3R,3'S,6'R)-Lutein (3'-Epilutein) and (3R,3'R)-Zeaxanthin", *Journal of Natural Products*, 66: 67-72 (2003), American Chemical Society and American Society of Pharmacognosy, USA.
Khachik F., et al., "Partial Synthesis of (3R,6'R)-α-Cryptoxanthin and (3R)-β-Cryptoxanthin from (3R,3'R,6'R)-Lutein", *Journal of Natural Products*, 70: 220-226 (2007), American Chemical Society and American Society of Pharmacognosy, USA.
Mayer H., "Synthesis of Optically Active Carotenoids and Related Compounds", *International Union of Pure and Applied Chemistry*, 51: 535-564 (1979), Pergamon Press Ltd., Great Britain, UK.
Müller R., et al., "Some Recent Advances in the Synthesis of Natural Carotenoids", *Food Chemistry*, 5: 15-45 (1980), Applied Science Publishers Ltd., London, England.
Rüttimann, A.V. and Mayer, H., "154. Synthese von optisch aktiven, natürlichen Carotinoiden and strukturell verwandten Naturprodukten, V. Synthese von (3R,3'R)-, (3S,3'S)- und (3R,3'S; meso)-Zeaxanthin durch asymmetrische Hydroborierung. Ein neuer Zugang zu optisch aktiven Carotinoidbausteinen," *Helvetica Chimica Acta*, 63: 1456-1462 (1980), Verlag Helvetica Chimica Acta, Switzerland.
Widmer E., et al., "87. Technical Procedures for the Syntheses of Carotenoids and Related Compounds from 6-Oxo-isophorone: Syntheses of (3R,3'R)-Zeaxanthin," *Helvetica Chimica Acta*, 73: 861-867 (1990), Verlag Helvetica Chimica Acta, Switzerland.

* cited by examiner

*Primary Examiner* — Sikarl Witherspoon

(74) *Attorney, Agent, or Firm* — Sterne, Kessler, Goldstein & Fox P.L.L.C.

(57) ABSTRACT

(3R,3'R,6'R)-Lutein and (3R,3'R)-zeaxanthin are two dietary carotenoids that are present in most fruits and vegetables commonly consumed in the US and accumulate in the human plasma, major organs, and ocular tissues. Another stereoisomer of (3R,3'R)-zeaxanthin that is not of dietary origin but is found in the human ocular tissues is (3R,3'S;meso)-zeaxanthin. There is growing evidence that these carotenoids play an important role in the prevention of age-related macular degeneration (AMD) that is the leading cause of blindness in the U.S. and the Western World. In view of the potential therapeutic application of dietary lutein, (3R,3'R)-zeaxanthin, and (3R,3'S;meso)-zeaxanthin, the industrial production of these carotenoids is of considerable importance. The present invention provides a process for the partial synthesis of (3R,3'R)-zeaxanthin and (3R,3'S;meso)-zeaxanthin from a readily accessible dehydration product of (3R,3'R,6'R)-lutein, namely, (3R)-3',4'-didehydro-β,β-caroten-3-ol [(3R)-3',4'-anhydrolutein]. The process involves regioselective hydroboration of (3R)-3',4'-anhydrolutein to a mixture of (3R,3'R)-zeaxanthin and (3R,3'S;meso)-zeaxanthin followed by separation of these carotenoids by enzyme-mediated acylation.

15 Claims, No Drawings

PROCESS FOR SYNTHESIS OF (3R,3'R)-ZEAXANTHIN AND (3R,3'S;MESO)-ZEAXANTHIN FROM (3R,3'R,6'R)-LUTEIN VIA (3R)-3',4'-ANHYDROLUTEIN

BACKGROUND OF THE INVENTION

1. Field of the Invention

The invention is in the field of organic chemistry. The invention relates to a process for the synthesis of (3R,3'R)-zeaxanthin and (3R,3'S;meso)-zeaxanthin from a dehydration product of (3R,3'R,6'R)-lutein, namely, (3R)-3',4'-didehydro-β,β-caroten-3-ol [(3R)-3',4'-anhydrolutein]. The process involves regioselective hydroboration of (3R)-3',4'-anhydrolutein to a mixture of (3R,3'R)-zeaxanthin and (3R, 3'S;meso)-zeaxanthin followed by separation of these carotenoids by enzyme-mediated acylation.

2. Related Art (3R,3'R,6'R)-Lutein and (3R,3'R)-zeaxanthin are two dietary carotenoids that are present in most fruits and vegetables commonly consumed in the US. These carotenoids accumulate in the human plasma, major organs, and ocular tissues [macula, retinal pigment epithelium (RPE), ciliary body, iris, lens]. In the past decade, numerous epidemiological and experimental studies have shown that dietary lutein and zeaxanthin play an important role in the prevention of age-related macular degeneration (AMD) that is the leading cause of blindness in the U.S. and Western World. Among the 7 stereoisomers of dietary (3R,3'R,6'R)-lutein, only (3R,3'S, 6'R)-lutein (3'-epilutein) has been detected in the human plasma and tissues. There are also two stereoisomers of (3R, 3'R)-zeaxanthin, these are: (3R,3'S;meso)-zeaxanthin and (3S,3'S)-zeaxanthin; these carotenoids are not of dietary origin. However, meso-zeaxanthin that is absent from human plasma, has been found in nearly all human ocular tissues. This carotenoid is presumably formed in the human eye tissues as a consequence of metabolic transformation of dietary (3R,3'R,6'R)-lutein (Khachik F. et al. *J. Invest. Ophthalmol. Vis. Sci.* 43, 3383-92, 2002). The chemical structures of these carotenoids are shown in Scheme 1. In view of the potential therapeutic application of dietary lutein, (3R,3'R)-zeaxanthin, and (3R,3'S;meso)-zeaxanthin, the industrial production of these carotenoids has received considerable attention. Due to its challenging total synthesis, dietary (3R,3'R,6'R)-lutein is isolated from saponified extracts of marigold flowers (*Tagete erecta*, variety *orangade*) and is commercially available as a nutritional supplement (Khachik, F. U.S. Pat. No. 5,382, 714, Jan. 17, 1995).

SCHEME 1

The chemical structures of dietary (3R,3'R,6'R)-lutein and (3R,3'R)-zeaxanthin and their stereoisomers found in humans.

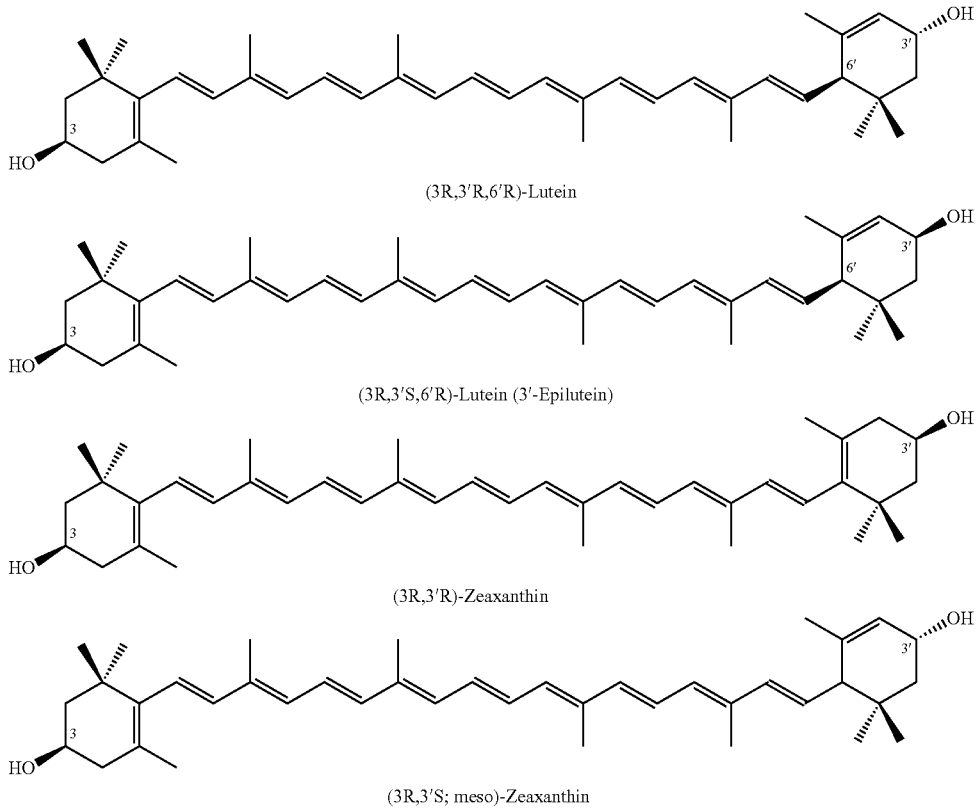

Although dietary (3R,3'R)-zeaxanthin is very widely distributed in Nature, its concentration in most readily available natural products is not sufficiently high for commercial production by extraction and isolation. Contrary to the situation with (3R,3'R,6'R)-lutein, numerous lengthy multistep processes have been developed for the total synthesis of (3R, 3'R)-zeaxanthin (Mayer, H. *Pure Appl. Chem.* 1979, 51, 535-564; Saucy, G. U.S. Pat. No. 4,153,615, May 8, 1979;

Rüttimann, A., Mayer, H. *Helv. Chim. Acta* 1980, 63, 1456-1462; Müller, R. K. et al. *Food Chem.* 1980, 5, 15-45; Widmer, E. et al. *Helv. Chim. Acta* 1990, 73, 861-867).

There are also several processes that convert the commercially available (3R,3'R,6'R)-lutein or crude saponified extracts of marigold flowers by base-catalyzed isomerization to optically inactive (3R,3'S;meso)-zeaxanthin (Torres-Cardona, M. D.; Quiroga, J. U.S. Pat. No. 5,523,494, Jun. 4, 1996; Bernhard, K, Giger, A. U.S. Pat. No. 5,780,693, Jul. 14, 1998; Rodriguez, G. A. International Patent to Prodemex, WO 99/03830, Jan. 28, 1999). In another process, (3R,3'R,6'R)-lutein is transformed into (3R,3'S;meso)-zeaxanthin similar to the above methods and the latter is oxidized to β,β-carotene-3,3'-dione followed by reduction with sodium or potassium borohydride to give a racemic mixture of (3R,3'R)-zeaxanthin, (3S,3'S)-zeaxanthin, and (3R,3'S;meso)-zeaxanthin (Virgili, S. et al. International Patent to Investigaciones Quimicas Y Farmaceuticas, WO 97/31894, Sep. 4, 1997). However, due to the low overall yield and the fact that the racemic mixture of (3RS,3'RS)-zeaxanthin was not resolved, this approach does not provide an attractive route for the industrial production of these carotenoids.

To circumvent the problems associated with the poor yield and the control of the stereochemistry in transformation of (3R,3'R,6'R)-lutein to (3R,3'R)-zeaxanthin, an efficient process has been reported by the author (Khachik, F. U.S. Pat. No. 6,818,798 B1, Nov. 16, 2004; Khachik, F. *J. Nat. Prod.* 2003, 66, 67-72). According to this process, lutein was first converted to a diastereomeric mixture of (3R,3'R,6'R)-lutein and (3R,3'S,6'R)-lutein (3'-epilutein) by acid-catalyzed epimerization followed by separation of these carotenoids by enzyme-mediated acylation. The resulting 3'-epilutein was then converted to (3R,3'R)-zeaxanthin by base-catalyzed isomerization. This process provided a convenient and alternative route to the total synthesis of dietary zeaxanthin.

The author now wishes to report yet another alternative method for transformation of dietary lutein to (3R,3'R)-zeaxanthin and (3R,3'S;meso)-zeaxanthin. These carotenoids are initially prepared as a diastereomeric mixture that is subsequently separated into individual compounds with the aim to provide access to both of these important nutrients.

BRIEF SUMMARY OF THE INVENTION

This invention takes advantage of the readily accessible (3R)-3',4'-didehydro-β,β-caroten-3-ol [(3R)-3',4'-anhydrolutein] as the starting material for preparation of (3R,3'R)-zeaxanthin and (3R,3'S;meso)-zeaxanthin. (3R)-3',4'-Anhydrolutein has been previously prepared as the major acid-catalyzed dehydration product of (3R,3'R,6'R)-lutein by the author as shown in Scheme 2 (Khachik, F. U.S. Pat. No. 7,115,786 B2, Oct. 3, 2006; Khachik, F. *J. Nat. Prod.* 2007, 70, 220-226).

SCHEME 2

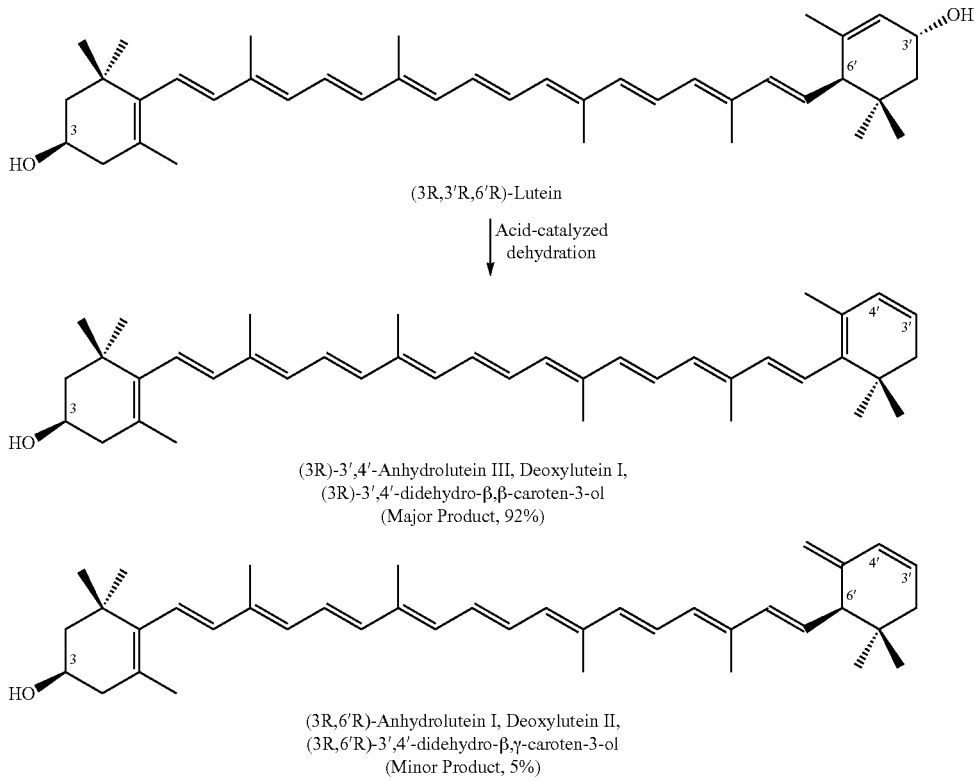

Acid-catalyzed dehydration of dietary (3R,3'R,6'R)-lutein according to the published procedures
(Khachik, F. U.S. Pat. No. 7,115,786 B2, October 3, 2006; Khachik, F. J. Nat. Prod. 2007, 70, 220-226).

(3R,3'R,6'R)-Lutein

Acid-catalyzed dehydration (3R)-3',4'-Anhydrolutein III, Deoxylutein I,
(3R)-3',4'-didehydro-β,β-caroten-3-ol
(Major Product, 92%)

(3R,6'R)-Anhydrolutein I, Deoxylutein II,
(3R,6'R)-3',4'-didehydro-β,γ-caroten-3-ol
(Minor Product, 5%)

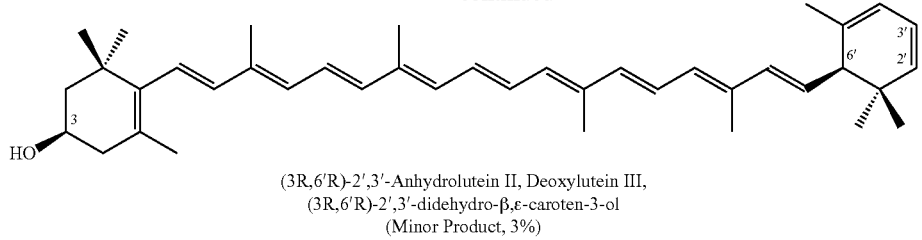

(3R,6'R)-2',3'-Anhydrolutein II, Deoxylutein III,
(3R,6'R)-2',3'-didehydro-β,ε-caroten-3-ol
(Minor Product, 3%)

The acid-catalyzed dehydration of (3R,3'R,6'R)-lutein, also results in the formation of two other minor dehydration products in addition to (3R)-3',4'-anhydrolutein; these are: (3R,6'R)-3',4'-didehydro-β,γ-caroten-3-ol [(3R,6'R)-anhydrolutein I] and (3R,6'R)-2',3'-didehydro-β,ε-caroten-3-ol [(3R,6'R)-2',3'-anhydrolutein II]. However, these carotenoids do not interfere with the conversion of (3R)-3',4'-anhydrolutein to (3R,3'R)-zeaxanthin and (3R,3'S;meso)-zeaxanthin. This transformation is accomplished by regioselective hydroboration of (3R)-3',4'-anhydrolutein followed by crystallization as shown in Scheme 3.

SCHEME 3

Transformation of (3R)-3',4'-anyhdrolutein to (3R,3'R)-zeaxanthin and (3R,3'S; meso)-zeaxanthin.

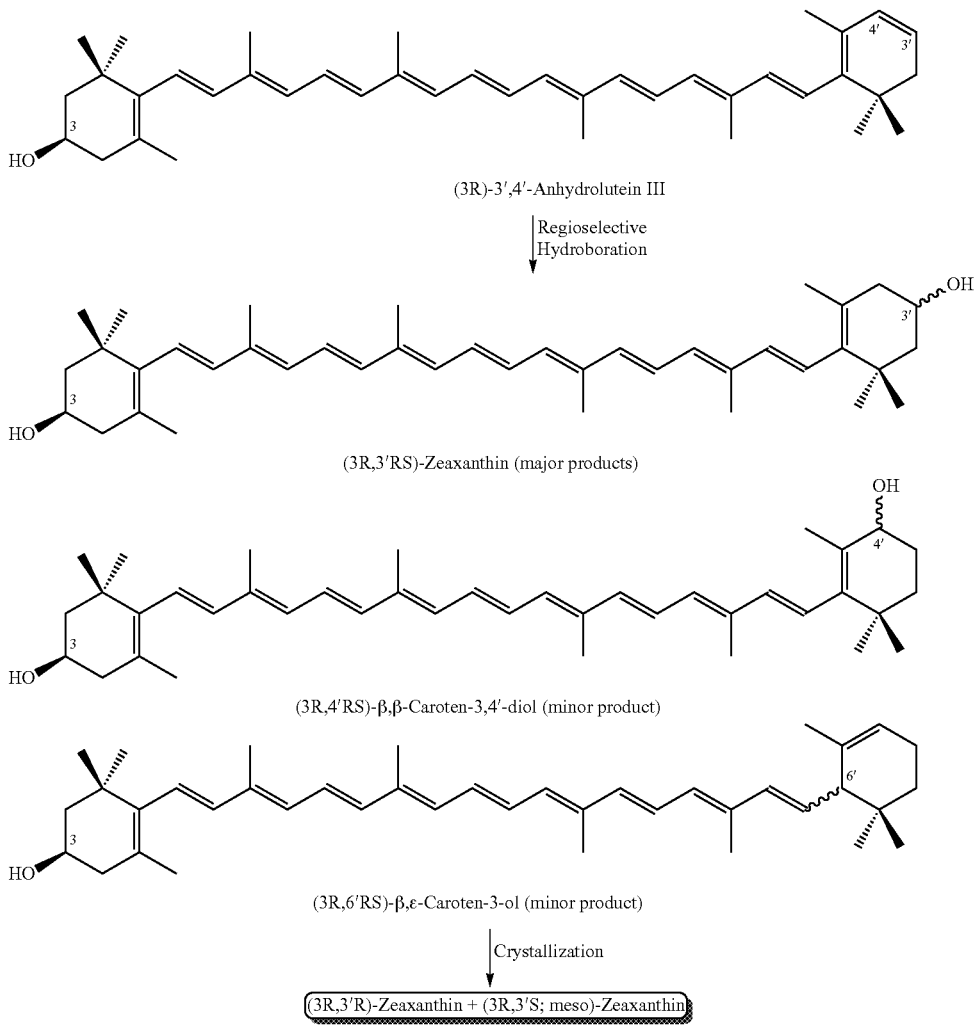

The regioselective hydroboration of (3R)-3',4'-anhydrolutein is carried out with a wide range of hydroborating reagents such as borane-tetrahydrofuran complex solution (BH₃.THF), borane-dimethyl sulfide complex solution (BH₃.SMe₂), borane-N,N-diethylaniline complex (BH₃.NPhEt₂), borane-N-ethyl-N-isopropylaniline complex (BH₃.NPhEtCHMe₂) (BACH-EI™), (−)-isopinocamphylborane-N,N,N',N'-tetramethyl-ethylenediamine (TMEDA) complex [(R)-ALPINE-BORAMINE™], and (−)-isopinocamphylborane-N,N,N',N'-tetramethyl-ethylenediamine (TMEDA) complex [(S)-ALPINE-BORAMINE™]. The reaction can be carried out in ether solvents such as tetrahydrofuran (THF), 1,2-dimethoxyethane (DME, ethylene glycol dimethyl ether), bis(2-methoxyethyl)ether (diglyme, diethylene glycol dimethyl ether), tert-butyl methyl ether (TBME)-diglyme, or in dichloromethane and 1,2-dimethoxyethane (CH₂Cl₂-DME). As shown in Scheme 3, the hydroboration of (3R)-3',4'-anhydrolutein, in addition to the desired products also results in the formation of minor amounts of (3R,4'RS)-β,β-caroten-3,4'-diol and (3R,6'RS)-β,ε-caroten-3-ol (α-cryptoxanthin). However, these minor side products can be readily removed by crystallization and do not contaminate the product. Although the diastereomeric mixture of (3R,3'R)-zeaxanthin and (3R,3'S;meso)-zeaxanthin can be directly used as a nutritional supplement, the present invention has developed a process for the separation of these carotenoids. This involves enzyme-mediated acylation of the mixture with immobilized lipase PS (*Pseudomonas cepacia*) or lipase AK (*Pseudomonas fluorescens*) in the presence of vinyl acetate which initially acylates these carotenoids into a mixture of (3R,3'R)-zeaxanthin-3-acetate and (3R,3'S)-zeaxanthin-3-acetate (Scheme 4). Further enzyme-mediate acylation of this mixture results in the formation of (3R,3'R)-zeaxanthin-3,3'-diacetate and (3R,3'S)-zeaxanthin-3-acetate. The separation of the zeaxanthin monoacylester and zeaxanthin diacylester is readily accomplished by column chromatography. After alkaline hydrolysis of zeaxanthin acyl esters, (3R,3'R)-zeaxanthin and (3R,3'S;meso)-zeaxanthin are obtained in 92% and 94% diastereomeric excess (de), respectively.

SCHEME 4

Separation of (3R,3'R)-zeaxanthin and (3R,3'S; meso)-zeaxanthin by enzyme-mediated acylation.

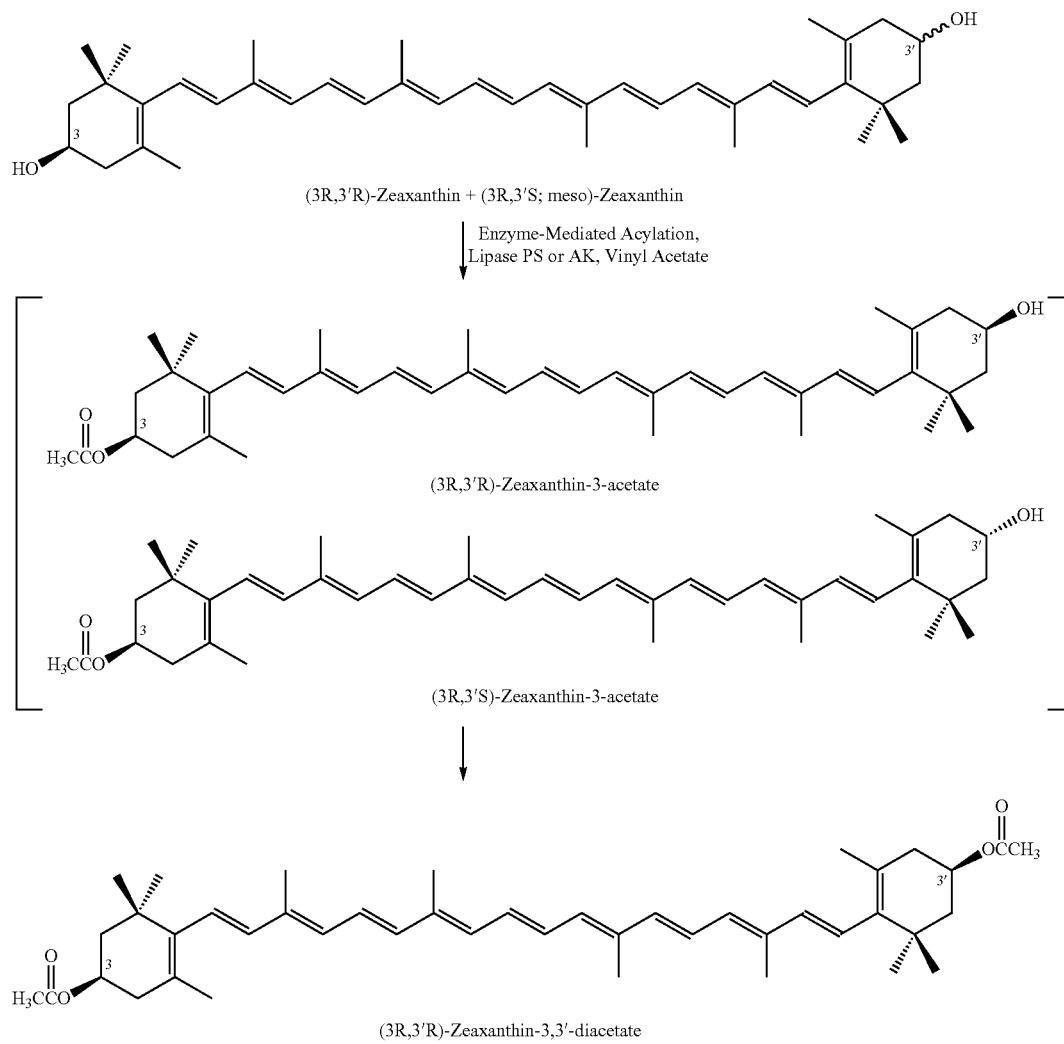

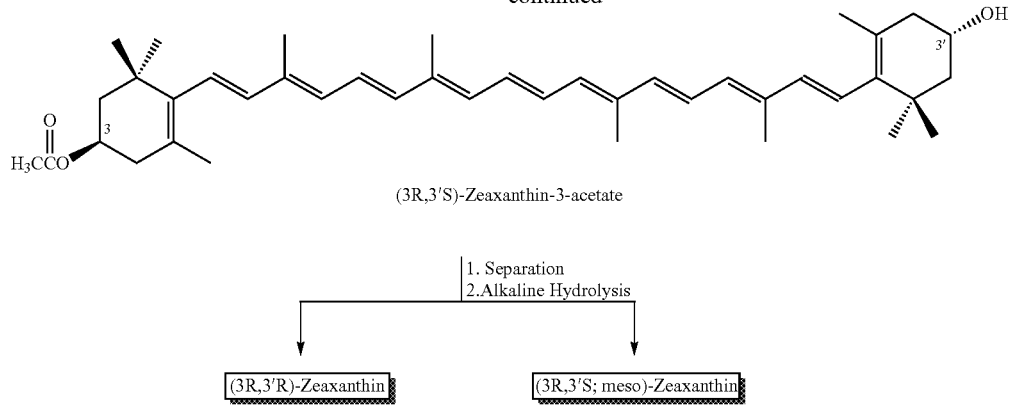

(3R,3'S)-Zeaxanthin-3-acetate

1. Separation
2. Alkaline Hydrolysis (3R,3'R)-Zeaxanthin    (3R,3'S; meso)-Zeaxanthin In one embodiment of the present invention, (3R)-3',4'-anhydrolutein is converted to a mixture of (3R,3'R)-zeaxanthin and (3R,3'S;meso)-zeaxanthin by regioselective hydroboration by reacting (3R)-3',4'-anhydrolutein with a hydroborating reagent, in a solvent, at a temperature ranging from 0-30° C. to obtain an isomeric mixture of (3R,3'R)-zeaxanthin and (3R,3'S;meso)-zeaxanthin as major products, in a ratio ranging from 1:1 to 3.4:1 and α-cryptoxanthin and (3R,4'RS)-β,β-caroten-3,4'-diol as two minor products. In some embodiments, the hydroborating reagent is selected from the group consisting of borane-tetrahydrofuran complex solution ($BH_3.THF$), borane-dimethyl sulfide complex solution ($BH_3.SMe_2$), borane-N,N-diethylaniline complex ($BH_3.NPhEt_2$), borane-N-ethyl-N-isopropylaniline complex ($BH_3.NPhEtCHMe_2$)(BACH-EI™), (−)-isopinocamphylborane-N,N,N',N'-tetramethyl-ethylenediamine (TMEDA) complex ((R)-ALPINE-BORAMINE™) and (+)-isopinocamphylborane-N,N,N',N'-tetramethyl-ethylenediamine (TMEDA) complex ((S)-ALPINE-BORAMINE™). In some embodiments, the hydroborating reagent is prepared in situ and then allowed to react with (3R)-3',4'-anhydrolutein. In one embodiment, the hydroborating agent is prepared by a method comprising adding a solution of methyl iodide (MeI) in an ether solvent to a solution of (3R)-3',4'-anhydrolutein in an ether solvent or in dichloromethane, in which sodium borohydride ($NaBH_4$) is suspended. In some embodiments, the hydroborating agent is prepared in an ether solvent is selected from the group consisting of tetrahydrofuran (THF), 1,2-dimethoxyethane (DME), bis(2-methoxyethyl)ether (diglyme), tert-butyl methyl ether (TBME) and a combination thereof, and the ether solvent optionally contains dichloromethane.

In one embodiment, a hydroborating reagent is allowed to react with (3R)-3',4'-anhydrolutein in an ether solvent or in dichloromethane at a temperature ranging from 0° C. to room temperature.

In one embodiment, a chiral hydroborating reagent is allowed to react with (3R)-3',4'-anhydrolutein wherein (3R, 3'R)-zeaxanthin is obtained as the major product and (3R,3'S; meso)-zeaxanthin is obtained as the minor product. In some embodiments, the chiral hydroborating reagent is (−)-isopinocamphylborane-N,N,N',N'-tetramethyl-ethylenediamine (TMEDA) complex ((R)-ALPINE-BORAMINE™).

In one embodiment, a mixture of (3R,3'R)-zeaxanthin and (3R,3'S;meso)-zeaxanthin is purified by crystallization to give a purity of greater than 95%. In some embodiments, the crystallization is carried out by a process comprising dissolving a mixture of (3R,3'R)-zeaxanthin and (3R,3'S;meso)-zeaxanthin in a solvent selected from the group consisting of dichloromethane, tetrahydrofuran (THF), tert-butyl methyl ether (TBME) and ethyl acetate, and adding a hydrocarbon solvent selected from the group consisting of pentane, hexane, heptane, cyclohexane and petroleum ether, followed by cooling to induce crystallization. In some embodiments, a mixture of (3R,3'R)-zeaxanthin and (3R,3'S;meso)-zeaxanthin is obtained from the crystallization.

In some embodiments, a mixture of (3R,3'R)-zeaxanthin and (3R,3'S;meso)-zeaxanthin with a purity of greater than 95% is used a nutritional supplement or a food coloring additive.

In one embodiment, a mixture of (3R,3'R)-zeaxanthin and (3R,3'S;meso)-zeaxanthin is separated by enzyme-mediated acylation by acylating a mixture of (3R,3'R)-zeaxanthin and (3R,3'S;meso)-zeaxanthin with immobilized lipase PS (*Pseudomonas cepacia*) or lipase AK (*Pseudomonas fluorescens*) in the presence of an acyl donor such as vinyl acetate at a temperature ranging from ambient to 50° C. in a solvent to obtain a mixture of (3R,3'R)-zeaxanthin-3,3'-diacetate and (3R, 3S")-zeaxanthin-3-acetate. In some embodiments, enzyme-mediated acylation is carried out in solvent such as ethyl acetate, or a ether solvent selected from the group consisting of ethyl ether, tetrahydrofuran (THF) and tert-butyl methyl ether (TBME).

In one embodiment, a mixture of (3R,3'R)-zeaxanthin-3,3'-diacetate and (3R, 3'S)-zeaxanthin-3-acetate obtained by enzyme-mediated acylation is separated by column chromatography using acetone, dichloromethane or ethyl acetate in combination with a hydrocarbon solvent selected from the group consisting of pentane, hexane, heptane, cyclohexane and petroleum ether to obtain (3R,3'R)-zeaxanthin-3,3'-diacetate and (3R,3'S)-zeaxanthin-3-acetate in 92% and 94% diastereomeric excess (de), respectively. In some embodiments, column chromatography is on silica gel.

In some embodiments, (3R,3"R)-zeaxanthin-3,3'-diacetate is saponified with alcoholic potassium hydroxide (KOH) or sodium hydroxide (NaOH) to obtain (3R,3'R)-zeaxanthin in 92% de or greater.

In some embodiments, (3R,3"S)-zeaxanthin-3-acetate is saponified with alcoholic potassium hydroxide (KOH) or sodium hydroxide (NaOH) to obtain (3R,3'S;meso)-zeaxanthin in 94% de or greater.

DETAILED DESCRIPTION OF THE INVENTION

Borane-ether ($BH_3.$ether) complex solutions were prepared fresh from sodium borohydride ($NaBH_4$) and methyl iodide (MeI) in ether solvents or in dichloromethane and an ether by a slight modification of a published method (Bell H. M. et al. *J. Org. Chem.* 34, 3923-26, 1969). All other chemicals and reagents including borane-dimethyl sulfide ($BH_3.SMe_2$), $BH_3.NPhEt_2$, $BH_3.NPhEtCHMe_2$, (R)-AL-PINE-BORAMIN™, and (S)-ALPINE-BORAMINE™ were commercially available and obtained from Aldrich Chemical Co. (St. Louis, Mo.). Lipase PS (*Pseudomonas cepacia*) and lipase AK (*pseudomonas fluorescens*) were from Amano Enzyme USA (Lombard, Ill.); these enzymes were immobilized according to a known procedure. All carotenoids were fully characterized by $^1H$ and $^{13}C$-NMR, MS, and UV-Vis, and circular dichroism (CD).

Hydroboration reactions were monitored by HPLC (eluent A) on a silica-based nitrile bonded (25-cm length×4.6 mm i.d.; 5-µm spherical particle) column (Waters Corporation, Milford, Mass.). The column was protected with a Brownlee nitrile bonded guard cartridge (3-cm length×4.6 mm ID; 5-µm particle size). Eluent A consisted of an isocratic mixture of hexane (75%), dichloromethane (25%), and methanol (0.6%). The column flow rate was 0.7 mL/min and the separations were monitored at 454 nm for zeaxanthin and 466 nm for (3R)-3',4'-anhydrolutein. In the order of elution, the HPLC retention times were: α-cryptoxanthin (10.37 min), (3R)-3',4'-anhydrolutein (10.74 min), (3R,4'RS)-β,β-caroten-3,4'-diol (28.71 min), and (3R,3'R)-zeaxanthin+(3R,3'S; meso)-zeaxanthin (coeluting peaks at 37.68 min).

The optical purity of (3R,3'R)-zeaxanthin and (3R,3'S; meso)-zeaxanthin was assessed by chiral HPLC (eluent B) on a CHIRALPAK® AD column (25-cm length×4.6 mm internal diameter) purchased from Chiral Technologies (Exton, Pa.). The column packing consisted of amylose tris-(3,5-dimethylphenylcarbamate) coated on 10 µm silica gel substrate and the column was protected with a silica gel guard cartridge (3-cm length×4.6 mm ID; 5 µm particle). For eluent B, a two pumps system with a combination of isocratic and gradient HPLC was employed that separated the stereoisomers of zeaxanthin at 450 nm. Pump One pumped a mixture of hexane (95%) and 2-propanol (5%) and pump Two pumped a mixture of hexane (85%), and 2-propanol (15%). At time zero, 95% solvents from pump One and 5% solvents from pump Two were pumped isocratically for 10 minutes. After 10 minutes, a linear gradient was run for 15 minutes during which the solvents from pump Two were linearly increased from 5% to 40% while that of pump One were reduced from 95% to 60%. At the end of each run, the column was re-equilibrated under the original isocratic conditions for 20 minutes. It should be noted that in addition to the separation of (3R,3'R)-zeaxanthin and (3R,3'S;meso)-zeaxanthin, this HPLC system can also separate (3S,3'S)-zeaxanthin. However, this stereoisomer of zeaxanthin is not formed according to the process described here.

The enzymatic acylation of (3R,3'R)-zeaxanthin and (3R,3'S;meso)-zeaxanthin were initially monitored by chiral HPLC employing the above eluent B until both zeaxanthins were monoacylated to (3R,3'R)-zeaxanthin-3-acetate and (3R,3'S)-zeaxanthin-3-acetate, respectively. To monitor the enzyme-mediate acylation of (3R,3'R)-zeaxanthin-3-acetate to (3R,3'R)-zeaxanthin diacetate, an isocratic mixture (eluent C) of hexane (95%) and isobutanol (5%) was used with the CHIRALPAK® AD column at a flow rate of 0.7 mL/min. Under these conditions, the monoacyl esters were separated and the course of the enzyme-mediated acylation could be easily monitored.

Purification of (3R)-3',4'-Anhydrolutein by Crystallization. A crude mixture (200 g) of (3R)-3',4'-anhydrolutein (84%, anhydrolutein III), (3R,6'R)-anhydrolutein I (10%), and (3R,6'R)-2',3'-anhydrolutein II (6%) was crystallized from dichloromethane (1000 mL) and ethanol (2000 mL) by stirring at room temperature for 6 h. After filtration and drying, the dark red crystals (70 g) were shown by HPLC to consist of (3R)-3',4'-anhydrolutein (92%), (3R,6'R)-anhydrolutein I (5%), and (3R,6'R)-2',3'-anhydrolutein II (3%). A second crystallization was performed by stirring 10 g of this mixture in dichloromethane (50 mL) for 30 min at room temperature followed by addition of ethanol (100 mL) and stirring for 2 h. After filtration and drying under high vacuum, the dark red crystals (8.2 g) were shown by HPLC to consist of (3R)-3',4'-anhydrolutein (96%), (3R,6'R)-anhydrolutein I (3%), and (3R,6'R)-2',3'-anhydrolutein II (1%). Hydroboration reactions were carried out with both, the anhydroluteins crystallized once and the anhydroluteins crystallized twice and the results were nearly identical. Based on the proton and carbon NMR data, no major differences between the profiles of the anhydroluteins crystallized once and anhydrolutein crystallized twice was observed.

Hydroboration of (3R)-3',4'-Anhydrolutein (Anhydrolutein III). In a preferred embodiment, a mixture of (3R)-3',4'-anhydrolutein (1 equiv.) and $NaBH_4$ (2 equiv.) in an ether solvent [20-30 mL/g of (3R)-3',4'-anhydrolutein] such as THF, DME, diglyme, TBME-diglyme or in $CH_2Cl_2$-DME is treated dropwise with a solution of methyl iodide (2 equiv.) in an ether solvent at ambient temperature under argon or nitrogen. The borane-ether complex generated in situ reacts with (3R)-3',4'-anhydrolutein at 20-25° C. very slowly with evolution of methane. The reaction time varies from 3-5 h and depends on the solubility of (3R)-3',4'-anhydrolutein in the solvent employed. During addition of MeI, occasional external cooling using a cold-water bath (≈10° C.) is necessary to maintain the temperature between 20-25° C. In addition to monitoring the reaction by HPLC (eluent A), the reaction can also be monitored by thin layer chromatography (TLC) employing hexane:acetone=7/3. The reaction mixture is then cooled down to −10° C. and the product is slowly treated with MeOH and stirred at this temperature for 30 min. The borane complex is then oxidized by dropwise addition of 3N NaOH followed by 30% $H_2O_2$ while the temperature is maintained at −10° C. After the addition is completed, the mixture is allowed to warm up to room temperature and stirred for 1 h. The product is then filtered and extracted with a water-immiscible organic solvent. After, drying over sodium sulfate and solvent evaporation, the product is crystallized from dichloromethane and hexane and dried under high vacuum.

In an alternative embodiment, $NaBH_4$ (2 equiv.) in an ether solvent such as THF, DME, diglyme, TBME-diglyme or in $CH_2Cl_2$-DME is treated dropwise with a solution of methyl iodide (2 equiv.) in an ether solvent at ambient temperature under argon or nitrogen to generate borane-ether complex. The solution is then cooled down to 0° C. and (3R)-3',4'-anhydrolutein (1 equiv.) in THF or $CH_2Cl_2$ is added and after stirring for 2 h at 0° C. and 2 h at room temperature, the product is worked up as described above.

The hydroboration may be similarly carried out with borane-N,N-diethylaniline complex [$BH_3.NPhEt_2$), borane-N-ethyl-N-isopropylaniline complex ($BH_3.NPhEtCHMe_2$) (BACH-EI™), (−)-isopinocamphylborane-N,N,N',N'-tetramethyl-ethylenediamine (TMEDA) complex [(R)-ALPINE-BORAMINE™], and (+)-isopinocamphylborane-N,N,N',N'-tetramethyl-ethylenediamine (TMEDA) complex [(S)-ALPINE-BORAMINE™]. The results of hydroboration of (3R)-3',4'-anhydrolutein with various reagents in a wide range of solvents are shown in Table 1. Due to the excellent solubility of (3R)-3',4'-anhydrolutein in THF, hydroboration in this solvent is preferred and gives the best results.

The reactions with $BH_3$.Ether and $BH_3.SMe_2$ in ether solvents and in $CH_2Cl_2$ in all cases resulted in complete conversion of (3R)-3',4'-anhydrolutein to the product. However, this was not found to be the case in hydroboration reactions with various borane-amine complexes in which 30-40% of (3R)-3',4'-anhydrolutein remained unreacted. The hydroboration of (3R)-3',4'-anhydrolutein in all cases also resulted in the formation of two minor side products that were isolated and identified from their NMR, UV-Vis, and MS as: α-cryptoxanthin and (3R, 4'RS)-β,β-caroten-3,4'-diol. These carotenoids were readily removed by crystallization of the crude product with $CH_2Cl_2$ and hexane. Instead of $CH_2Cl_2$, other solvents such as ethyl acetate, or ethers such as THF or TBME can be employed. Similarly, hexane can be replaced with other hydrocarbon solvents such as pentane, heptane, or cyclohexane. Unless otherwise stated, the yields shown in Table 1 are based on the isolated yields of the purified mixture of (3R,3'R)-zeaxanthin and (3R,3'S;meso)-zeaxanthin that were obtained after crystallization.

in Scheme 4. The course of the reaction is monitored by chiral HPLC (eluent B) that show the gradual conversion of zeaxanthins to their corresponding monoacetates. When the reaction is allowed to proceed for another 24 h at room temperature, (3R,3'R)-zeaxanthin-3-acetate is acylated to (3R,3'R)-zeaxanthin-3,3'-diacetate while (3R,3'S)-zeaxanthin-3-acetate remains unchanged. The progress of this reaction can be best monitored by HPLC employing eluent C that separates these zeaxanthin monoacetates. The overall reaction time can be substantially reduced if the enzyme-mediated acylation is carried out at 40-45° C. After the removal of the enzyme, the crude product is separated by column chromatography (hexane:acetone, 95:5 to 90:10) on n-silica gel. Due to the difference in their solubility and chromatographic properties, (3R,3'R)-zeaxanthin-3,3'-diacetate is almost immediately eluted from the column whereas (3R,3'S)-zeaxanthin-3-acetate elutes later from the column. The alkaline hydrolysis of these individually pure mono- and diacetates of zeaxanthin is carried out in an alcoholic solution of KOH or

TABLE 1

Results of hydroboration of (3R)-3',4'-anhydrolutein in different solvents.

| Hydroborating Reagent-Solvent | Distribution of Carotenoids in the Crude Products (%) | | | Yield of Zeaxanthin[a] (%) |
|---|---|---|---|---|
| | Zeaxanthin (3R,3'R) + (3R,3'S; meso) | α-Cryptoxanthin | (3R,4'RS)-β,β-caroten-3,4'-diol | |
| $BH_3$-THF | 92 | 6 | 2 | 75 |
| $BH_3$-DME | 85 | 10 | 5 | 57 |
| $BH_3$-Diglyme | 84 | 12 | 4 | 45 |
| $BH_3$-TBME-Diglyme | 87 | 9 | 4 | 55 |
| $BH_3$-DME-$CH_2Cl_2$ | 85 | 10 | 5 | 58 |
| $BH_3$-$Me_2S$—$CH_2Cl_2$ | 59 | 35 | 6 | 40 |
| $H_3B$—$NPhEt_2$-THF | 46 | 0.0 | 6 | 46[b] |
| $H_3B$—$NPhEtCHMe_2$-THF | 78 | 10 | 12 | 56 |
| (R)-ALPINE-BORAMINE ™-THF | 68 | 25 | 7 | 40[c] |
| (S)-ALPINE-BORAMINE ™-THF[b] | 65 | 27 | 8 | 40[d] |

[a]If not specified, yield refers to crystallized zeaxanthin that does not contain any α-cryptoxanthin nor (3R,4'RS)-β,β-caroten-3,4'-diol;
[b]48% of (3R)-3',4'-anhydrolutein remained unreacted and the yield was determined by HPLC;
[c](3R,3'R):(3R,3'S; meso) = 77:23 (54% diastereomeric excess, de);
[d](3R,3'R):(3R,3'S; meso) = 43:57.

Particularly interesting were the hydroboration of (3R)-3',4'-anhydrolutein with (±)-isopinocamphylborane-N,N,N',N'-tetramethyl-ethylenediamine (TMEDA) complex [(R)- and (S)-ALPINE-BORAMINE™] that are well-established reagents for stereospecific hydroboration of alkenes (H. C. Brown, *J. Organometallic Chem*, 500, 1995, 1-19). With (−)-isopinocamphylborane-N,N,N',N'-tetramethyl-ethylenediamine (TMEDA) complex [(R)-ALPINE-BORAMINE™] (3R,3'R)-zeaxanthin was obtained in 54% diastereomeric excess (de) while (+)-isopinocamphylborane-N,N,N',N'-tetramethyl-ethylenediamine (TMEDA) complex [(S)-ALPINE-BORAMINE™] did not show any significant diastereoselectivity and the de of (3R,3'S;meso)-zeaxanthin was only 14%.

Separation of (3R,3'R)-Zeaxanthin and (3R,3'S;meso)-Zeaxanthin by Enzyme-Mediated Acylation. In a preferred embodiment, a mixture of (3R,3'R)-zeaxanthin and (3R,3'S; meso)-zeaxanthin in ethyl acetate or ether solvents such as ethyl ether, THF, or TBME is stirred with immobilized lipase PS (*Pseudomonas cepacia*) or lipase AK (*Pseudomonas fluorescens*) in the presence of an acyl donor such as vinyl acetate at ambient temperature. This initially acylates these carotenoids within the first 24 h into a mixture of (3R,3'R)-zeaxanthin-3-acetate and (3R,3'S)-zeaxanthin-3-acetate as shown NaOH to afford (3R,3'R)-zeaxanthin and (3R,3'S;meso)-zeaxanthin in 92% and 94% diastereomeric excess (de), respectively.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

Example 1

Hydroboration of (3R)-3',4'-Anhydrolutein with $BH_3$-THF at Ambient Temperature (3R)-3',4'-Anhydrolutein (5 g, 9.08 mmol) and $NaBH_4$ (0.72 g, 19.02 mmol) were transferred into a 250 mL flask equipped with an argon inlet, a thermometer, a mechanical stirrer, and an addition funnel. Dry THF (130 mL) was added and the mixture was stirred under argon. The flask was immersed in a cold-water bath (≈10-15° C.) and a solution of methyl iodide (1.2 mL, 2.736 g, 19.28 mmol) in dry THF (10 mL) was added dropwise at ambient temperature (20-25° C.) in 10 min during which gas evolution began and a thick dark red paste was formed. After 2 h, no detectable amount of (3R)-3',4'-anhydrolutein was shown by HPLC (eluent A) to be present. The mixture was cooled down to −10° C., methanol (15 mL) was added drop wise, and the mixture was stirred until all the solids were dissolved. This was followed by sequential addition of 3N NaOH (15 mL) and 30% $H_2O_2$ (15 mL) while maintaining the temperature at −10° C. The mixture was allowed to warm up to room temperature and stirred for 1 h; during this period the temperature rose to 29° C. and then dropped back to ambient temperature (25° C.). The solids were removed by filtration and the product was partitioned between water (150 mL) and $CH_2Cl_2$ (150 mL). The organic layer was washed with water (2×100 mL), dried over sodium sulfate, and filtered. The HPLC analysis (eluent A) of the crude product showed the presence of (3R,3'R)-zeaxanthin and (3R,3'S;meso)-zeaxanthin as coeluting peaks (92%), α-cryptoxanthin (6%), and (3R, 4'RS)-β,β-caroten-3,4'-diol (2%). The solution of the crude product was concentrated under reduced pressure and the dark orange residue was crystallized from $CH_2Cl_2$ (100 mL) and hexane (150 mL). After cooling at 0-5° C. for several hours, the orange crystals were collected by filtration and dried under high vacuum overnight to give a mixture of (3R,3'R)-zeaxanthin and (3R,3'S;meso)-zeaxanthin (3.87 g, 6.80 mmol; 75%). The HPLC analysis of the product did not show the presence of any other carotenoids or impurities and the $^1H$- and $^{13}C$-NMR spectra of zeaxanthins were consistent with the reported literature data.

Example 2

Hydroboration of (3R)-3',4'-Anhydrolutein with $BH_3$-THF at 0° C.

Methyl iodide (1.2 mL, 2.736 g, 19.28 mmol) in dry THF (10 mL) was added dropwise to a suspension of $NaBH_4$ (0.72 g, 19.02 mmol) in THF (50 mL) under argon. After stirring for 40 min at room temperature (R.T.), the mixture was cooled down to 0° C. and a solution of (3R)-3',4'-anhydrolutein (5 g, 9.08 mmol) in dry THF (80 mL) was added dropwise while maintaining the temperature at 0° C. After stirring for 2 h at 0° C. and 2 h at R.T., the mixture was cooled down to −10° C., methanol (15 mL) was added dropwise, and the mixture was stirred until all the solids were dissolved. This was followed by sequential addition of 3N NaOH (15 mL) and 30% $H_2O_2$ (15 mL) while maintaining the temperature at −10° C. The mixture was allowed to warm up to room temperature and stirred for 1 h. The product was worked up as in example 1 and crystallized from $CH_2Cl_2$ and hexane to give a mixture of (3R,3'R)-zeaxanthin and (3R,3'S;meso)-zeaxanthin (3.98 g, 7.00 mmol; 77%).

Example 3

Hydroboration of (3R)-3',4'-Anhydrolutein with $BH_3$-DME

To a mixture of (3R)-3',4'-anhydrolutein (1 g, 1.82 mmol) and $NaBH_4$ (0.145 g, 3.83 mmol) in dry 1,2-dimethoxyethane (DME, 30 mL) under argon was added a solution of methyl iodide (0.24 mL, 0.547 g, 3.86 mmol) in dry DME (2 mL) at room temperature (20-25° C.) in 5 min. Occasional cooling with a cold-water bath (10-15° C.) was necessary to maintain the temperature between 20-25° C. After 3 h, a thick dark red paste was formed and no detectable amount of (3R)-3',4'-anhydrolutein was shown by HPLC (eluent A) to be present. The mixture was cooled down to −10° C., methanol (3 mL) was added, and the mixture was stirred until all the solids were dissolved. This was followed by sequential addition of 3N NaOH (3 mL) and 30% $H_2O_2$ (3 mL) while maintaining the temperature at −10° C. The mixture was allowed to warm up to room temperature and stirred for 1 h. The solids were removed by filtration and the product was partitioned between water (40 mL) and ethyl acetate (40 mL). The organic layer was washed with water (2×100 mL), dried over sodium sulfate, and filtered. After solvent evaporation, the product was crystallized from ethyl acetate (30 mL) and hexane (45 mL) to give a mixture of (3R,3'R)-zeaxanthin and (3R,3'S;meso)-zeaxanthin (0.59 g, 1.04 mmol; 57%).

Example 4

Hydroboration of (3R)-3',4'-Anhydrolutein with $BH_3$-DME in $CH_2Cl_2$

To a mixture of (3R)-3',4'-anhydrolutein (1 g, 1.82 mmol) and $NaBH_4$ (0.145 g, 3.83 mmol) in $CH_2Cl_2$ (30 mL) under argon was added a solution of methyl iodide (0.24 mL, 0.547 g, 3.86 mmol) in dry 1,2-dimethoxyethane (DME, 3 mL) at room temperature (20-25° C.) in 5 min. After 4 h, a thick orange paste was formed and no detectable amount of (3R)-3',4'-anhydrolutein was shown by HPLC to be present. The mixture was cooled down to −10° C. and was sequentially treated with methanol (3 mL), 3N NaOH (3 mL), 30% $H_2O_2$ (3 mL), and worked up as described in Example 3. Crystallization from $CH_2Cl_2$ (20 mL) and hexane (30 mL) gave a mixture of (3R,3'R)-zeaxanthin and (3R,3'S;meso)-zeaxanthin (0.58 g, 1.02 mmol; 56%).

Example 5

Hydroboration of (3R)-3',4'-Anhydrolutein with $BH_3$—$SMe_2$ in $CH_2Cl_2$

To a solution of (3R)-3',4'-anhydrolutein (1 g, 1.82 mmol) in $CH_2Cl_2$ (30 mL) under argon was added a 2M solution of borane-methyl sulfide (1.9 mL, 3.8 mmol) at room temperature (20-25° C.) in 5 min. After 3 h, a thick orange paste was formed and no detectable amount of (3R)-3',4'-anhydrolutein was shown by HPLC to be present. The mixture was cooled down to −10° C. and was sequentially treated with methanol (3 mL), 3N NaOH (3 mL), 30% $H_2O_2$ (3 mL), and worked up as described in Example 3. Crystallization from $CH_2Cl_2$ (20 mL) and hexane (30 mL) gave a mixture of (3R,3'R)-zeaxanthin and (3R,3'S;meso)-zeaxanthin (0.414 g, 0.728 mmol; 40%).

Example 6

Hydroboration of (3R)-3',4'-Anhydrolutein with $BH_3$—$NPhEt_2$ in THF

To a solution of (3R)-3',4'-anhydrolutein (1 g, 1.82 mmol) in THF (30 mL) under argon was added a solution of $BH_3$—$NPhEt_2$ (0.84 mL, 0.770 g, 4.72 mmol) at room temperature (20-25° C.). After 3 h, the mixture was cooled down to −10° C. and was treated with methanol (3 mL), 3N NaOH (3 mL), 30% $H_2O_2$ (3 mL), and worked up with ethyl acetate as described in Example 3. The HPLC analysis (eluent A) of the crude product showed the presence of unreacted (3R)-3',4'- anhydrolutein (48%), (3R,3'R)-zeaxanthin and (3R,3'S; meso)-zeaxanthin as coeluting peaks (46%), and (3R, 4'RS)-β,β-caroten-3,4'-diol (6%).

Example 7

Hydroboration of (3R)-3',4'-Anhydrolutein with BH$_3$—NPhEtCHMe$_2$ in THF

To a solution of (3R)-3',4'-anhydrolutein (1 g, 1.82 mmol) in THF (30 mL) under argon was added a 2.0 M solution of BH$_3$—NPhEtCHMe$_2$ (2.4 mL, 4.80 mmol) in THF at room temperature (20-25° C.) in 5 min. After 3 h, the mixture was cooled down to −10° C. and was treated with methanol (3 mL), 3N NaOH (3 mL), 30% H$_2$O$_2$ (3 mL), and worked up with ethyl acetate as described in Example 3. The HPLC analysis (eluent A) of the crude product showed the presence of (3R,3'R)-zeaxanthin and (3R,3'S;meso)-zeaxanthin as coeluting peaks (78%) as well as (3R, 4'RS)-β,β-caroten-3,4'-diol (12%) and α-cryptoxanthin (10%). Purification of the product by column chromatography (hexane:acetone, 95:5 to 70:30) gave a mixture of (3R,3'R)-zeaxanthin and (3R,3'S;meso)-zeaxanthin (0.58 g, 1.02 mmol; 56%).

Example 8

Hydroboration of (3R)-3',4'-Anhydrolutein with (−)-Isopinocamphylborane-N,N,N'-tetramethylethylenediamine (TMEDA) complex [(R)-ALPINE-BORAMINE™] in THF To a solution of (R)-ALPINE-BORAMINE™ (0.33 g, 0.793 mmol) in THF (5 mL) was added a solution of boron trifluoride-diethyl etherate (0.2 mL, 0.224 g, 1.58 mmol) at room temperature under argon and the mixture was stirred for 1 h. The mixture was then cooled down to 0° C. and a solution of (3R)-3',4'-anhydrolutein (0.25 g, 0.44 mmol) in THF (5 mL) was added. After 3 h, the mixture was sequentially treated with methanol (0.5 mL), 3N NaOH (0.5 mL), 30% H$_2$O$_2$ (0.5 mL), and worked up with ethyl acetate as described in Example 3. The HPLC analysis (eluent A) of the crude product showed the presence of (3R,3'R)-zeaxanthin and (3R,3'S;meso)-zeaxanthin as coeluting peaks (68%) as well as (3R, 4'RS)-β,β-caroten-3,4'-diol (25%) and α-cryptoxanthin (7%). Purification of the product by column chromatography (hexane:acetone, 95:5 to 70:30) gave a mixture of (3R,3'R)-zeaxanthin and (3R,3'S;meso)-zeaxanthin (0.100 g, 0.176 mmol; 40%). Chiral HPLC analysis (eluent B) of the product revealed the ratio of (3R,3'R)-zeaxanthin:(3R,3'S;meso)-zeaxanthin=77:23 corresponding to a de of 54% for the (3R,3'R)-isomer.

Example 9

Hydroboration of (3R)-3',4'-Anhydrolutein with (+)-Isopinocamphylborane-N,N,N',N'-tetramethylethylenediamine (TMEDA) complex [(S)-ALPINE-BORAMINE™] in THF To a solution of (R)-ALPINE-BORAMINE™ (0.33 g, 0.793 mmol) in THF (5 mL) was added a solution of boron trifluoride-diethyl etherate (0.2 mL, 0.224 g, 1.58 mmol) at room temperature under argon and the mixture was stirred for 1 h. The mixture was then cooled down to 0° C. and a solution of (3R)-3',4'-anhydrolutein (0.25 g, 0.44 mmol) in THF (5 mL) was added. After 3 h, the mixture was treated with methanol (0.5 mL), 3N NaOH (0.5 mL), 30% H$_2$O$_2$ (0.5 mL), and worked up with ethyl acetate as described in Example 3. The HPLC analysis (eluent A) of the crude product showed the presence of (3R,3'R)-zeaxanthin and (3R,3'S;meso)-zeaxanthin as coeluting peaks (65%) as well as (3R,4'RS)-β,β-caroten-3,4'-diol (27%) and α-cryptoxanthin (8%). Purification of the product by column chromatography (hexane:acetone, 95:5 to 70:30) gave a mixture of (3R,3'R)-zeaxanthin and (3R,3'S;meso)-zeaxanthin (0.100 g, 0.176 mmol; 40%). Chiral HPLC analysis (eluent B) of the product revealed the ratio of (3R,3'R)-zeaxanthin:(3R,3'S;meso)-zeaxanthin=43:57 corresponding to a de of 14% for the (3R,3'S;meso)-isomer.

Example 10

Separation of (3R,3'R)-Zeaxanthin and (3R,3'S;meso)-Zeaxanthin by Enzyme-Mediated Acylation with Lipase PS (*Pseudomonas cepacia*)

Immobilization of Lipase PS (*Pseudomonas cepacia*). Lipase PS (3.0 g) and diatomaceous earth (HYFLO SUPER CEL®) (10 g) were mixed and 10 mL of phosphate buffer (pH=7.0) was added. After mixing for 15 min, the paste was spread out on a Petri dish and allowed to dry for 2 days in the presence of air. The same procedure was employed for the immobilization of Lipase AK (*Pseudomonas fluorescens*).

A mixture of (3R,3'R)-zeaxanthin and (3R,3'S;meso)-zeaxanthin (0.6 g, 1.06 mmol) in THF (20 mL) was treated with immobilized lipase PS (0.6 g) and vinyl acetate (3 mL) and the mixture was stirred at room temperature under argon. The course of the reaction was monitored by chiral HPLC (eluent B). After 24, all of zeaxanthins were acylated to (3R,3'R)-zeaxanthin-3-acetate and (3R,3'S)-zeaxanthin-3-acetate. Stirring continued for another 24 h and the progress of the reaction was monitored by chiral HPLC employing eluent C. When all the (3R,3'R)-zeaxanthin-3-acetate was acylated to (3R,3'R)-zeaxanthin-3,3'-diacetate (total of 48 h), the enzyme was removed by filtration and the solvent was evaporated under reduced pressure to give 0.65 g of a crude product. Column chromatography of the residue on n-silica gel (hexane:acetone, 95:5 to 90:10) gave two main fractions that were identified from their mass and NMR spectra as (3R,3'R)-zeaxanthin-3,3'-diacetate (0.274 g, 0.42 mmol) and (3R,3'S)-zeaxanthin-3-acetate (0.244 g, 0.40 mmol).

Hydrolysis of (3R,3'R)-Zeaxanthin-3,3'-Diacetate. A solution of (3R,3'R)-zeaxanthin-3,3'-diacetate (0.274 g, 0.42 mmol) in THF (10 mL) was stirred with 10% methanolic KOH (2 mL) under argon. After 1 h, the product was partitioned between water (20 mL) and CH$_2$Cl$_2$ (20 mL). The organic layer was removed and washed with water (2×20 mL), dried over Na$_2$SO$_4$, and evaporated to dryness to give (3R,3'R)-zeaxanthin (0.221 g, 0.39 mmol). The product was shown by chiral HPLC (eluent B) to consist of (3R,3'R)-zeaxanthin (96%) and (3R,3'S;meso)-zeaxanthin (4%) corresponding to a diasteromeric excess (de) of 92% for the (3R,3'R)-isomer.

Hydrolysis of (3R,3'S)-Zeaxanthin-3-Acetate. A solution of (3R,3'S)-zeaxanthin-3-acetate (0.20 g, 0.33 mmol). in THF (10 mL) was stirred with 10% methanolic KOH (2 mL) under argon. After 1 h, the product was partitioned between water (20 mL) and CH$_2$Cl$_2$ (20 mL). The organic layer was removed and washed with water (2×20 mL), dried over Na$_2$SO$_4$, and evaporated to dryness to give (3R,3'S;meso)-zeaxanthin (0.176 g, 0.31 mmol). The product was shown by chiral HPLC (eluent B) to consist of (3R,3'S;meso)-zeaxanthin (97%) and (3R,3'R)-zeaxanthin (3%) corresponding to a diasteromeric excess (de) of 94% for the (3R,3'S;meso)-isomer.

What is claimed is:

1. A process for converting (3R)-3',4'-anhydrolutein to a mixture of (3R,3'R)-zeaxanthin and (3R,3'S;meso)-zeaxanthin by regioselective hydroboration comprising reacting (3R)-3',4'-anhydrolutein with a hydroborating reagent, in a solvent, at a temperature ranging from 0-30° C. to obtain an isomeric mixture of (3R,3'R)-zeaxanthin and (3R,3'S;meso)-zeaxanthin as major products, in a ratio ranging from 1:1 to 3.4:1 and a-cryptoxanthin and (3R,4'RS)-β,β-caroten-3,4'-diol as two minor products.

2. The process of claim 1, wherein said hydroborating reagent is selected from the group consisting of borane-tetrahydrofuran complex solution ($BH_3.THF$), borane-dimethyl sulfide complex solution ($BH_3.SMe_2$), borane-N,N-diethylaniline complex ($BH_3.NPhEt_2$), borane-N-ethyl-N-isopropylaniline complex ($BH_3.NPhEtOHMe_2$), (−)-isopinocamphylborane-N,N,N;N'-tetramethylethylenediamine (TMEDA) complex and (+)-isopinocamphylborane-N,N,N', N'-tetramethyl-ethylenediamine (TMEDA) complex.

3. The process of claim 2, wherein said hydroborating reagent is prepared in situ and then allowed to react with (3R)-3',4'-anhydrolutein.

4. The process of claim 3, wherein said hydroborating agent is prepared by a method comprising adding a solution of methyl iodide (MeI) in an ether solvent to a solution of (3R)-3',4'-anhydrolutein in an ether solvent or in dichloromethane, in which sodium borohydride ($NaBH_4$) is suspended.

5. The process of claim 4, wherein said ether solvent is selected from the group consisting of tetrahydrofuran (THF), 1,2-dimethoxyethane (DME), bis(2-methoxyethyl)ether (diglyme), tert-butyl methyl ether (TBME) and a combination thereof, wherein said ether solvent optionally also contains dichloromethane.

6. The process of claim 1, wherein said hydroborating reagent is allowed to react with (3R)-3',4'-anhydrolutein in an ether solvent or in dichloromethane at a temperature ranging from 0° C. to room temperature.

7. The process of claim 1, wherein said hydroborating reagent is chiral and wherein (3R,3'R)-zeaxanthin is obtained as the major product and (3R,3'S;meso)-zeaxanthin is obtained as the minor product.

8. The process of claim 7, wherein said chiral hydroborating reagent is (−)-isopinocamphylborane-N,N,N',N-tetramethylethylenediamine (TMEDA) complex.

9. The process of claim 1, further comprising crystallizing said mixture of (3R,3'R)-zeaxanthin and (3R,3'S;meso)-zeaxanthin to give a purity of greater than 95%.

10. The process of claim 9, wherein said crystallizing is carried out by a process comprising dissolving said mixture in a solvent selected from the group consisting of dichloromethane, tetrahydrofuran (THF), tert-butyl methyl ether (TBME) and ethyl acetate, and adding a hydrocarbon solvent selected from the group consisting of pentane, hexane, heptane, cyclohexane and petroleum ether, followed by cooling to induce crystallization.

11. A process for separating a mixture of (3R,3'R)-zeaxanthin and (3R,3'S;meso)-zeaxanthin by enzyme-mediated acylation comprising acylating a mixture of (3R,3'R)-zeaxanthin and (3R,3'S:meso)-zeaxanthin with immobilized lipase PS (*Pseudomonas cepacia*) or lipase AK (*Pseudomonas fluorescens*) in the presence of an acyl donor at a temperature ranging from ambient to 50° C. in ethyl acetate, or a ether solvent selected from the group consisting of ethyl ether, tetrahydrofuran (THF) and tert-butyl methyl ether (TBME) to obtain a mixture of (3R,3'R)-zeaxanthin-3,3'-diacetate and (3R,3'S)-zeaxanthin-3-acetate; and separating said mixture of (3R,3'R)-zeaxanthin-3,3'-diacetate and (3R,3'S)-zeaxanthin-3-acetate by column chromatography using acetone, dichloromethane or ethyl acetate in combination with a hydrocarbon solvent selected from the group consisting of pentane, hexane, heptane, cyclohexane and petroleum ether to obtain (3R,3'R)-zeaxanthin-3,3'-diacetate and (3R,3'S)-zeaxanthin-3-acetate in 92% and 94% diastereomeric excess (de), respectively.

12. The process of claim 11, wherein said acyl donor is vinyl acetate.

13. The process of claim 11, wherein said column chromatography is on silica gel.

14. The process of claim 11, further comprising saponifying (3R,3'R)-zeaxanthin-3,3'-diacetate with alcoholic potassium hydroxide (KOH) or sodium hydroxide (NaOH) to obtain (3R,3'R)-zeaxanthin in 92% de or greater.

15. The process of claim 11, further comprising saponifying (3R,3'S)-zeaxanthin-3-acetate with alcoholic potassium hydroxide (KOH) or sodium hydroxide (NaOH) to obtain (3R,3'S;meso)-zeaxanthin in 94% de or greater.

* * * * *